United States Patent

Rustin et al.

[11] Patent Number: 6,133,322
[45] Date of Patent: Oct. 17, 2000

[54] QUINONE DERIVATIVES FOR TREATING OR PREVENTING DISEASES ASSOCIATED WITH IRON OVERLOAD

[75] Inventors: Pierre Rustin; Agnès Rötig, both of Paris, France

[73] Assignee: Institut National de la Sante et de la Recherche Medicale (INSERM), Paris, France

[21] Appl. No.: 09/315,585

[22] Filed: May 20, 1999

[30] Foreign Application Priority Data

Oct. 29, 1998 [EP] European Pat. Off. ............. 98402703

[51] Int. Cl.[7] ..................................... A61K 31/12
[52] U.S. Cl. ........................... 514/689; 514/678
[58] Field of Search ...................... 514/689, 678

[56] References Cited

U.S. PATENT DOCUMENTS

| | | | |
|---|---|---|---|
| 4,056,613 | 11/1977 | Bertazzoli et al. | 424/94 |
| 4,778,798 | 10/1988 | Brasey | 514/277 |
| 4,959,212 | 9/1990 | Stancesco et al. | 424/94.1 |
| 5,916,925 | 11/1999 | Higuchi et al. | 514/678 |

*Primary Examiner*—Raymond Henley, III
*Attorney, Agent, or Firm*—Alston & Bird LLP

[57] ABSTRACT

A method of treating or preventing a disorder resulting from a mitochondrial dysfunction induced by an iron overload including Friedreich Ataxia, hypertrophic cardiomyopathy, Hallervorden-Spatz disease, sideroblastic anemia by administering an effective amount of an ubiquinone derivative such as idebenone, decylubiquiqnone, coenzyme Q2, coenzyme Q4, and coenzyme Q6, either alone or in conjunction with a second therapeutic agent or a non-reducing antioxidant.

18 Claims, 4 Drawing Sheets

| Parameters | 10/97 | Patient 1 07/98 | Improvement | 06/98 | Patient 6 10/98 | Improvement | 06/98 | Patient 7 10/98 | Improvement |
|---|---|---|---|---|---|---|---|---|---|
| Septal thickness (cm) | 1.74 | 1.12 | -36% | 1.51 | 1.02 | -32% | 1.50 | 1.03 | -31% |
| LV posterior wall thickness (cm) | 1.18 | 1.04 | -12% | 1.07 | 0.86 | -20% | 1.41 | 1.3 | -8% |
| LV mass index (g) | 145 | 114 | -21% | 215 | 151 | -30% | 408 | 279 | -32% |

B)

| Patients | Sex | Age (yrs) | Duration of treatment (mths) | Fatigue, muscle weakness | Tremor, clumsiness (hand-writing) | Dysarthria, slurred speech | Asynergia, dysmetria (finger-nose test) | Dysdiadocho-kinesia (rapid alternating movements) | Gait ataxia | Abolished deep tendon reflexes |
|---|---|---|---|---|---|---|---|---|---|---|
| 1 | F | 7.8 | 6 | ⌐ | ⌐ | 0 | ⌐ | ⌐ | ® | ® |
| 2 | F | 10.7 | 8 | ⌐ | ⌐ | 0 | ® | ® | ⌐ | ® |
| 3 | F | 14.3 | 8 | ⌐ | ⌐ | 00 | ⌐ | ® | ® | ® |
| 4 | F | 14.3 | 9 | ⌐ | ® | 0 | ® | ® | ⌐ | ® |
| 5 | F | 13.2 | 8 | ⌐ | ⌐ | ⌐ | ⌐ | ® | ® | ® |
| 6 | F | 18.9 | 4 | ⌐ | ® | 0 | ® | ⌐ | ® | ® |
| 7 | M | 21.4 | 4 | ® | ® | ⌐ | ⌐ | ⌐ | ⌐ | ® |
| Total observable improvement: | | | | 6/7 | 5/7 | 1/7 | 4/7 | 1/7 | 2/7 | 0/7 |

QUINONE DERIVATIVES FOR TREATING OR PREVENTING DISEASES ASSOCIATED WITH IRON OVERLOAD

FIELD OF THE INVENTION

The present invention relates to a method of treating or preventing disorders associated with a intracellular iron overload, and more particularly Friedreich Ataxia (FRDA), Hallervorden-Spatz disease, or sideroblastic anemia associated with iron overload. More particularly, the invention relates to the administration of quinone derivatives such as coenzyme $Q_{10}$ (ubiquinone) and its short-chain analogues (coenzyme $Q_4$ and idebenone) to protect the heart and brain of FRDA patients from iron-induced injury.

BACKGROUND OF THE INVENTION

The Friedreich ataxia (FRDA) is a frequent autosomal degenerative disease (1/30,000 live birth). It is characterized by spinocerebellar degeneration resulting in progressive limb and gait ataxia with lack of tendon reflexes in the legs and in pyramidal syndrome of the inferior limbs, and by hypertrophic cardiomyopathy. Geoffroy et al., Clinical description and roentgenologic evaluation of patients with Friedreich's ataxia, Can. J. Neurol. Sci. 3, 279–286 (1976); Harding, Friedreich's ataxia: a clinical and genetic study of 90 families with an analysis of early diagnostic criteria and intrafamilial clustering of clinical features, Brain, 104, 598–620 (1981). The disease gene has been mapped to chromosome 9q13 and encodes an ubiquitous 210-aminoacid protein, frataxin, targeted to the mitochondria. Chamberlain et al., Genetic homogeneity of the Friedreich ataxia locus on chromosome 9, Am. J. Human. Genet., 44, 518–521 (1989); Campuzano et al., Friedreich's ataxia: autosomal recessive disease caused by an intronic GAA triplet repeat expansion, Science, 271, 1423–1427 (1996); KoutnikovA et al., Studies of human, mouse and yeast homologue indicate a mitochondrial function for the frataxin, Nature Genet., 16, 345–351 (1997); Priller et al., Frataxin gene of Friedreich's ataxia is targeted to mitochondria, Ann. Neurol, 42, 265–269 (1997); Babcock et al., Regulation of mitochondrial iron accumulation by Yfh 1p, a putative homologue of fraxatin, Science, 276, 1709–1712 (1997); Foury et al., Deletion of the yeast homologue of the human gene associated with Friedreich's ataxia elicits iron accumulation in mitochondria, FEBS Lett., 411, 373–377 (1997); Wilson et al., Respiratory deficiency due to loss of mitochondrial DNA in yeast lacking the frataxin homologue, Nature Genet., 16, 352–357 (1997). FRDA is primarily caused by a GAA repeat expansion in the first intron of the fraxatin gene, which accounts for 98% of mutant alleles. Campuzano et al., Friedreich's ataxia: autosomal recessive disease caused by an intronic GAA triplet repeat expansion, Science, 271, 1423–1427 (1996). Yet, the tissue-specific expression of the disease remains unexplained and no animal model is presently available in FRDA.

The inventors have recently reported in Rötig et al., Aconitase and mitochondrial iron-sulphur protein defiency in Friedreich ataxia, Nature Genet., 17, 215–217 (1997) a deficient activity of the iron-sulphur (Fe-S) cluster containing proteins (ISP) in endomyocardical biopsies of FRDA patients, namely complexes I, II and III of the mitochondrial respiratory chain and aconitase, which cytosolic activity regulates cell iron homeostasis. Accordingly, ISPs have been shown to rapidly lose their catalytic activity in both FRDA patients and yeast strains carrying a deleted frataxin gene counterpart.

ISPs have been found to be remarkably sensitive to oxygen free radicals. Schoonen et al., Respiratory failure and stimulation of glycolysis in Chinese hamster ovary cells exposed to normobaric hyperoxia, J. Biol. Chem., 265, 1118–1124 (1990); Gardner et al., Aconitase is a sensitive and critical target of oxygen poisoning in cultured mammalian cells in rat lungs, Proc. Natl. Acad. Sci. USA, 91, 12248–12252 (1994); Li et al., Dilated cardiomyopathy and neonatal lethality in mutant mice lacking manganese superoxide dismutase, Nature Genet., 11, 376–381 (1996).

At the same time, iron has been found to be deposited in heart tissues of FRDA patients. Sanchez-Casis et al., Pathology of the heart in Friedreich's ataxia: review of the literature and report of one case, Can. J. Neurol. Sci., 3, 349–354 (1977).

Considering the remarkable sensitivity of ISPs to oxygen free radicals on the one hand and the reported iron deposit in heart tissues of FRDA patients on the other, the inventors have hypothesized that:

i) mitochondrial iron accumulation in FRDA is the consequence of the permanent activation of a mitochondrial iron import system, triggered by the decreased amount of frataxin, normally acting as a down regulator of mitochondrial iron uptake, and that ii) mitochondrial iron overload in FRDA would cause oxydative stress and an alteration of mitochondrial functions, through the iron-catalyzed Fenton chemistry. This posed the question of whether anti-oxidants would prevent the oxidative stress resulting from iron overload and alleviate the subsequent mitochondrial dysfunction.

Using an in vitro system, the inventors found that reduced (but not oxidized) iron was responsible for peroxidation of lipid membrane components and loss of membrane and soluble ISP activity, that antioxidants such as superoxide dismutase (SOD) and catalase were unable to prevent the iron-induced damages of the membrane components, and that reducing antioxidants such as ascorbate and glutathione were enhancing these damages.

SUMMARY OF THE INVENTION

The inventors have surprisingly discovered that ubiquinone derivatives, after reduction in situ by the mitochondrial respiratory chain, efficiently protected the membrane lipids as well as membrane and soluble ISP activity from iron-induced oxidative damages.

The present invention relates to a method for treating disorders resulting from a mitochondrial dysfunction induced by an iron overload by administering to a patient suffering of said disorder an effective amount of an ubiquinone derivative. Such disorders are generally associated with diseases which include, but are not limited to, Friedreich Ataxia (FRDA), Hallervorden-Spatz disease, sideroblastic anemia associated with iron overload, and more generally any disease comprising impairment of the mitochondrial function resulting from an intracellular iron overload.

The term "ubiquinone derivatives", as used herein, encompasses natural ubiquinones (coenzyme Q) as well as their structural analogs having a reversibly reducible quinone ring, with a lipophilic side chain.

All ubiquinones derivatives are potentially suitable for use in the method of the invention, since the quinone ring accounts for the similar properties of these molecules. However, for a better diffusion across tissues, short-chain quinones such as idebenone, decylubiquiqnone, coenzyme Q2, coenzyme Q4, coenzyme Q6 are preferred. A particularly preferred quinone is idebenone. Idebenone is already used as a nootropic drug, hypothesized to improve brain metabolism and promoting secretion of nerve growth factor (NGF).

These and other objects of the invention will be apparent to those of ordinary skill in the art in view of the additional detailed description provided below relating to preferred embodiments of the invention.

BRIEF DESCRIPTION OF THE FIGURES

FIG. 1 depicts the effect of iron on membrane lipids, complex II and aconitase activities in human heart homogenates.

A: Iron-induced peroxidation of membrane lipids, using cis-parinaric acid (c-PN) as a fluorescent probe:
   trace a: reduced iron;
   trace b: oxidized iron.

B: Activity of complex II (trace a), measured as succinate quinone dichlorophenolindophenol reductase (DCPIP) in nmol DCPIP reduced/min/mg protein:
   trace a: control;
   trace b: 5 nM reduced iron+1 nM EDTA;
   trace c: 5 nM reduced iron.

C: Aconitase activity, measured by the accumulation of aconitate in the presence of citrate in nmol aconitate/min/mg protein:
   trace a: control;
   trace b: 5 nM reduced iron;
   trace c: 250 $\mu$M desferrioxamine;
   trace d: 5 nM reduced iron+250 $\mu$M desferrioxamine.

FIG. 2 depicts the protective effect of reduced quinones on membrane lipids, complex II and aconitase activities in human heart homogenates.

A: Effect of idebenone on iron-induced lipoperoxidation.
   trace a: preincubation of heart homogenate with 60 $\mu$M oxidized idebenone for 3 min;
   trace b: preincubation of heart homogenate with 1 $\mu$M reduced idebenone (10 mM succinate-reduced) and 59 $\mu$M oxidized idebenone for 3 min immediately before addition of c-PN;
   trace c: preincubation of heart homogenate with 9 $\mu$M reduced idebenone (10 mM succinate-reduced) and 51 $\mu$M oxidized idebenone for 3 min.

B: Effect of $CoQ_{10}$ on iron-induced lipoperoxidation.
   trace a: preincubation of heart homogenate with 8 $\mu$M oxidized $CoQ_{10}$ for 3 min;
   trace b: preincubation of heart homogenate with 8 $\mu$M of oxidized $CoQ_{10}$+10 mM succinate for 3 min;
   Inset:
   trace a: preincubation of liposomes loaded with $CoQ_{10}$ for 3 min without succinate;
   trace b: preincubation of liposomes loaded with $CoQ_{10}$ for 3 min with 10 mM succinate;

C: Effect of the redox statute of idebenone on iron-induced inactivation of complex II measured in nmol DCPIP reduced/min/mg protein:
   trace a: preincubation of heart homogenate for 3 min with 10 mM succinate alone;
   trace b: preincubation of heart homogenate for 3 min with 60 $\mu$M idebenone alone;
   trace c: preincubation of heart homogenate for 3 min with 10 mM succinate+60 $\mu$M idebenone.

D: Effect of the redox statute of $CoQ_{10}$ on iron-induced inactivation of aconitase measured in nmol aconitate/min/mg protein:
   trace a: preincubation of heart homogenate for 3 min with 5 nM $Fe^{2+}$, 8 $\mu$M $CoQ_{10}$, and 10 mM succinate+additional 3 min incubation with 250 $\mu$M desferrixamine;
   trace b: preincubation of heart homogenate for 6 min with 250 $\mu$M desferrixamine;
   trace c: preincubation of heart homogenate for 3 min with 5 nM $Fe^{2+}$ and 8 $\mu$M $CoQ_{10}$+additional 3 min incubation with 250 $\mu$M desferrixamine.

FIG. 3A shows the improvement in three patients by a decrease in the septal and left ventricle posterior wall thickness;

FIG. 3B summarizes the changes in cerebellar ataxia noted by parents and uninformed teachers.

DESCRIPTION OF THE PREFERRED EMBODIMENTS OF THE INVENTION

In order to elucidate the mechanism of the damages that iron load causes to ISPs and to devise new strategies for future therapeutic trials, the inventors developed an in vitro system using human heart homogenates to mimic the action of iron on mitochondrial ISPs and to test the potentially protective effect of various substances.

Using this system the inventors have shown that reduced iron triggered a rapid lipoperoxidation and loss of complex II activity, which is not inhibited by superoxide dismutase (SOD) and catalase. Oxidized iron alone does not have the same effect; however, this effect is observed when a reducing antioxidant such as ascorbate is added to oxidized iron. Further, in association with water-soluble iron chelators (EDTA, desferrioxamine) reduced iron caused a marked loss of water-soluble aconitase activity.

Without being limited by theory, it is believed that positively charged iron is retained by negatively charged membrane phospholipids, thereby causing an intra-membranous accumulation of oxygen free radicals which cannot be prevented by water-soluble superoxide dismutase (SOD) and catalase. On the other hand, iron overload could be removed from mitochondrial membranes by water-soluble chelators (EDTA, desferrioxamine) thus triggering the production of oxygen free radicals in the aqueous phase. In vivo, phosphate-containing compounds present in the mitochondrial matrix, such as ADP and ATP, could act as natural chelators and might play a role in the partitioning of iron overload between mitochondrial membranes and matrix. For this reason, both membrane ISPs and soluble matrix aconitase are expected to be targeted by oxygen free radicals in FRDA (10).

Also, reducing antioxidant drugs such as ascorbate and glutathione, which are likely to reduce iron, as well as water soluble chelators should be regarded as potentially harmful in patients with iron overload.

Among other numerous antioxidant drugs, the inventors selected ubiquinone derivatives, namely coenzyme $Q_{10}$ (ubiquinone) and 2 of its short-chain analogues (coenzyme $Q_4$ and idebenone) for further investigations.

They found that when reduced in situ by the respiratory chain, they efficiently protected lipid membrane components as well as soluble and membrane ISP from iron-induced damages.

In contrast with antioxidants such as ascorbate, the reduced ubiquinone derivatives do not increase the reduction status of iron-loaded mitochondria. Further, due to their lipophilicity they can prevent intra-membranous accumulation of oxygen free radicals; they also believed to indirectly protect soluble aconitase by causing reoxidation of reduced iron.

While the quinone ring accounts for the similar redox properties of these molecules, and their ability in protecting the mitochondrial function against iron-induced injury, length and composition of the side chain modulate their lipophilicity and diffusion across tissues. Ernster et al., Biochemical, physiological and medical aspects of ubiquinone function, Biochim. Biophys. Acta., 1271, 195–204 (1995); Gillis et al., Idebenone, Drugs & Aging, 5, 133–152 (1994); Nz-Nagy, Chemistry, toxicology, pharmacology and pharmacokinetics of idebenone: a review, Arch. Gerontol. Geriart., 11, 177–186 (1990). Although we found that various quinone analogues equally protected ISPs against iron-induced injury, those quinones that readily cross the brain-blood barrier, such as short-chain quinones (such as idebenone, decylubiquiqnone, coenzyme Q2, coenzyme Q4, coenzyme Q6), are preferred.

All ubiquinones derivatives are potentially suitable for use in the method of the invention, since the quinone ring accounts for the similar properties of these molecules. Ubiquinone derivatives, in their oxidized form, particularly suitable for use in the present invention include those having the formula:

wherein R is linear or branched, saturated or unsaturated, aliphatic hydrocarbon or alcohol chain from 5 to 50 carbon atoms, preferably 10 to 30 carbon atoms.

For a better diffusion across tissues, short-chain quinones such as idebenone (6-(10-hydroxydecyl)-2,3-dimethoxy-5-methyl-1,4-benzoquinone), decylubiquiqnone, coenzyme Q2, coenzyme Q4, coenzyme Q6 are preferred. A particularly preferred quinone is idebenone, which in its oxidized form has the following formula:

Idebenone is already used as a nootropic drug, hypothesized to improve brain metabolism and promoting secretion of nerve growth factor (NGF). Idebenone is described in the specification of Japanese Patent Examined Publication No. 3134/1987 filed by Takeda Chemical Industries, Ltd.

Coenzyme Q may be represented by the following formula, where for Q2 n=2; Q4 n=4 and Q6 n=6:

Decylubiquinone has the following formula:

In the present invention, the oxidized form of ubiquinone is administered and, through reduction in situ by the respiratory chain, results in production of the active reduced form having the formula wherein R is linear or branched, saturated or unsaturated, aliphatic hydrocarbon or alcohol chain from 5 to 50 carbon atoms, preferably 10 to 30 carbon atoms.

In the method of the present invention, a significant release of cardiac symptoms has been observed after the administration of an effective amount of ubiquinone derivative after 4 months of regular administration. Since these derivatives are almost devoid of toxicity, they may be administered as long as necessary required, and even over the lifetime of the patient if required.

An effective amount of ubiquinone derivative is administered to the patient. Amounts of 1 mg/kg/day to 25 mg/kg/day, or even more, are suitable for administration. A dosage of 5 mg/kg/day of ubiquinone derivative given orally has proved its efficiency in controlling the cardiomyopathy in the patients. However, due to the innocuousness of these ubiquinone derivatives higher dosages, up to 25 mg/kg/day, may be used if necessary. This quantity may be administered once a day, of if desired it may be divided into two or more administrations.

In a trial, five FRDA patients were given idebenone. A 4 to 9 month regime of idebenone administration resulted in a significant decrease in myocardial hypertrophy and in a limited but detectable improvement of muscle strength, tremor, hand clumsiness, gait ataxia and asynergia/dysmetria. Further, the decrease of left ventricle thickness in three patients was observed.

The ubiquinone derivative may be administered by any suitable means known to one of ordinary skill in the art. In a preferred embodiment, the ubiquinone derivatives are administered orally. In another embodiment parenteral administration is used.

Formulations of ubiquinone derivative suitable for oral administration, may be in the form of discrete units, such as capsules, cachets, or tablets, or in the form of a powder or granules for reconstitution. Formulations suitable for oral or parenteral administration may be in the form of a solution or a suspension or an emulsion in an aqueous liquid or non-aqueous liquid.

All these formulations may be prepared by any of the methods known in the art of pharmacology.

In addition to containing the ubiquinone derivative and the standard and well known pharmaceutical carriers and/or excipients, all of the above formulations may contain at least another therapeutically-active substance, such as α-tocopherol, or additional non-reducing antioxidant molecules.

The present invention is illustrated by the Examples that follow, without being limited, however, to the specific details of these Examples.

Example 1

Iron-Induced Damages to Membrane Lipids, Complex II and Aconitase Activities in Human Heart Homogenates Methods Human heart homogenates were used as an in vitro model to mimic the action of iron on mitochondrial ISPs and to test the potentially protective effect of various substances.

These homogenates were prepared under low iron-chelating conditions using the procedures described in Rustin P. et al., Biochemical and molecular investigations in respiratory chain deficiencies, Clin. Chim. Acta., 228, 35–51 (1994). Briefly, homogenate from frozen human heart was obtained surgically and prepared at ice-melting temperature in a 0.1 M Tris-HCI buffer (pH 7.3) by five strokes of hand-driven ground glass potter using the procedures described in Sanchez-Casis et al., Pathology of the heart in Friedreich's ataxia: review of the literature and report of one case, Can. J. Neurol. Sci., 3, 349–354 (1977). After filtering through a 90 μm nylon net, homogenate was sampled and frozen at −80° C. for enzyme studies.

The endogenous antioxidant defenses of heart mitochondria were neutralized by simple dilution, and free access of iron to its specific targets was achieved by freeze-thaw disrupting mitochondrial membranes.

Lipoperoxidation, a marker of non-specific peroxidative damages caused to membrane components, was monitored in the presence of either reduced or oxidized iron. Cis-parinaric acid (c-PN) was used as a fluorescent probe for lipoperoxidation (15,16). Measurements were performed in a 37° C. thermostated quartz cell, magnetically stirred, and containing 2 ml 0.1 M Tris-HCI buffer (pH 7.3) using a LS540B Spectrofluorimeter (Perkin-Elmer, England). Excitation: 318 nm; 5 nm band-pass Emission: 410 nm; 5 nm band-pass.

The activities of two enzymes specifically targeted in FRDA, namely membrane-bound respiratory chain complex II and soluble (mitochondrial plus cytosolic) aconitases, were monitored under either low or high iron chelating conditions, in the presence of either reduced or oxidized iron. Complex II activity was measured on freeze-thaw heart homogenate as the dichlorophenolindophenol quinone reductase (DCPIP) (14). Aconitase activity in heart homogenate, corresponding to the combined mitochondrial and cytosolic enzyme activities, was measured by following the aconitate accumulation at 240 nm in the presence of citrate (6). All measurements were performed using a DW2000 Aminco Spectrophotometer (SLM, USA) in a 37° C. thermostated quartz cell, magnetically stirred, and containing 2 ml 0.1 M Tris-HCI buffer (pH 7.3).

Results

Figure 1A:
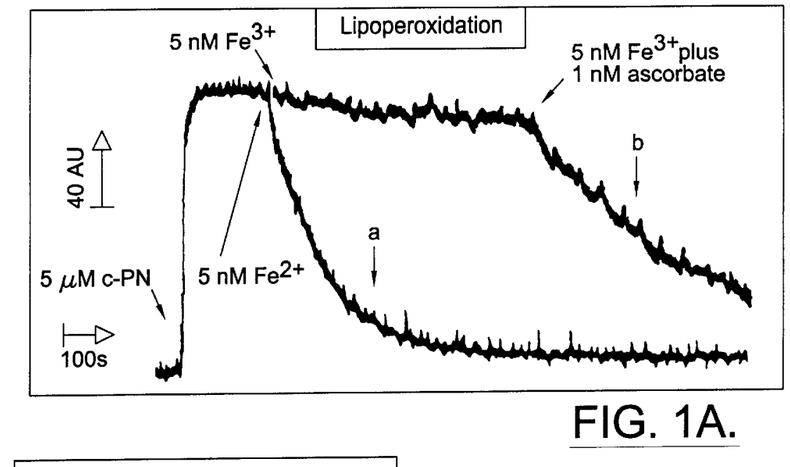

The results are shown in FIG. 1 and Table 1. In FIG. 1, which depicts the effect of iron on membrane lipids, complex II and aconitase activities in human heart homogenates, FIG. 1A shows iron-induced peroxidation of membrane lipids, using cis-parinaric acid (c-PN) as a fluorescent probe, with trace a depicting the reduced iron and trace b the oxidized iron.

Figures 1B, 1C:
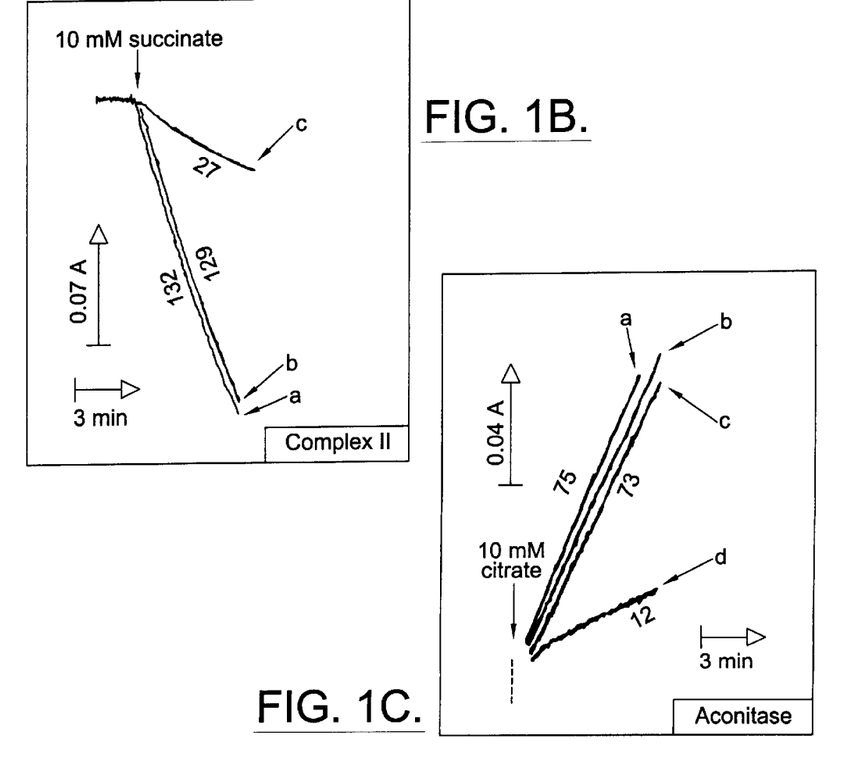

FIG. 1B shows the activity of complex II (trace a), measured as succinate quinone dichlorophenolindophenol reductase (DCPIP) wherein trace a is the control, trace b is 5 nM reduced iron+1 nM EDTA, and trace c is 5 nM reduced iron, with the numbers along the traces nmol DCPIP reduced/min/mg protein.

FIG. 1C shows aconitase activity, measured by the accumulation of aconitate in the presence of citrate with trace a as the control, trace b is 5 nM reduced iron, trace c is 250 μM desferrioxamine, and trace d is 5 nM reduced iron+250 μM desferrioxamine, with the numbers along the traces nmol aconitate/min/mg protein.

FIG. 1A shows that the iron-induced peroxidation of membrane lipids is fully dependent on the redox status of added iron. Reduced iron triggered an immediate peroxidation of the membrane lipid (trace a). Under similar conditions, oxidized iron did not significantly after membrane lipids (upper part of trace b). A subsequent addition of an ascorbate/$Fe^{3+}$ mixture induced an active peroxidation (lower part of trace b).

FIG. 1B shows that the activity of complex II (trace a) is strongly affected by a 1 min incubation of heart homogenate with 5 nM reduced iron (trace c). Complex II activity was fully protected by 1 nM EDTA added to the iron-supplemented incubation medium (trace b).

FIG. 1C shows that aconitase activity (trace a), was not affected by a 10 min incubation of the heart homogenate sample added with 5 nM reduced iron (trace b). Conversely 250 μM desferrioxamine added to the iron-supplemented incubation medium caused a significant loss of aconitase activity (80%; trace d). No inhibition of aconitase activity by desferrioxamine was observed in the absence of iron (trace c). Similar results were obtained when EDTA was substituted for desferrioxamine (not shown).

The values of lipids peroxidation, complex II activity, and aconitase activity listed in Table 1 are percent of the rates measured in the absence of iron, and represent the mean ±1 SD of three different measurements. Experiments were carried out as indicated above. nm: not measured; SOD:superoxide dismutase.

TABLE 1

| | Iron-induced damages to: | | |
|---|---|---|---|
| Condition | Lipids | Complex II | Aconi-tases |
| 5 nM $Fe^{2+}$ | −72 ± 3 | −75 ± 3 | −3 ± 1 |
| 5 nM $Fe^{3+}$ | 0 ± 0.2 | −2 ± 1 | 0 ± 0.1 |
| 2 mM EDTA | nm | 0 ± 0.1 | 0 ± 0.1 |
| 120 μM desferrioxamine | nm | nm | 0 ± 0.5 |
| 5 nM $Fe^{2+}$ + 2 nM EDTA | −2 ± 1 | +12 ± 2 | −83 ± 3 |
| 5 nM $Fe^{2+}$ + 120 μM desferrioxamine | 0 ± 1 | nm | −92 ± 4 |
| 5 nM $Fe^{2+}$ + 6 U SOD + 6 U catalase | −55 ± 2 | −68 ± 3 | nm |
| 5 nM $Fe^{2+}$ + 2 nM EDTA + 6 U SOD | nm | nm | −75 ± 1 |

TABLE 1-continued

| | | Iron-induced damages to: | |
|---|---|---|---|
| Condition | Lipids | Complex II | Aconitases |
| 5 nM Fe$^{2+}$ + 2 nM EDTA + 6 U catalase | nm | nm | −46 ± 2 |
| 5 nM Fe$^{2+}$ +2 nM EDTA + 6 U SOD + 6 U catalase | nm | nm | +5 ± 1 |
| 5 nM Fe$^{2+}$ + 250 μM desferri-oxamine + 6 U SOD + 6 U catalase | nm | nm | −6 ± 1 |

The above results show that reduced iron, tested as ferrous chloride, resulted in a rapid lipoperoxidation (FIG. 1A, trace a) and a significant loss of complex II activity (more than 75%) after a 1 min incubation of heart homogenates with 5 nM Fe$^{2+}$ (FIG. 1B, trace c; Table 1). On the other hand, no damage was observed when an oxidized iron solution, ferric chloride, was substituted for ferrous ions (FIG. 1A, trace b; Table 1).

Addition of an ascorbate/Fe$^{3+}$ mixture triggered a significant lipoperoxidation (FIG. 1A, trace b).

While ferrous ions alone failed to cause any damage to aconitase addition of water-soluble chelators in the presence of reduced iron, led to a significant loss of aconitase activity (FIG. 1C, trace d; Table 1). This effect is reverted by water-soluble anti-oxidants (500, catalase). By contrast, water-soluble chelators protected membrane lipid components and membrane-bound Fe-S respiratory chain enzyme proteins against iron-induced injury (FIGS. 1A and B; Table 1). One possible explanation for this is that iron chelators shifted iron from the negatively charged lipid phase to the aqueous phase, and changed the nature of the targeted enzymes rather than they reduced iron toxicity. The protective effects of superoxide dismutase and catalase supported involvement of Fenton chemistry in the damages caused by iron plus chelators (EDTA or desferrioxamine) to aconitase activity (Table 1).

Example 2

Quinone Protection of Membrane Lipids, Complex II and Aconitase Against Iron-Induced Damages Lipids peroxidation, complex II activity, and aconitase activity were monitored according to the methods of example 1 above. The results are shown in FIG. 2 and Table 2.

Figure 2A:
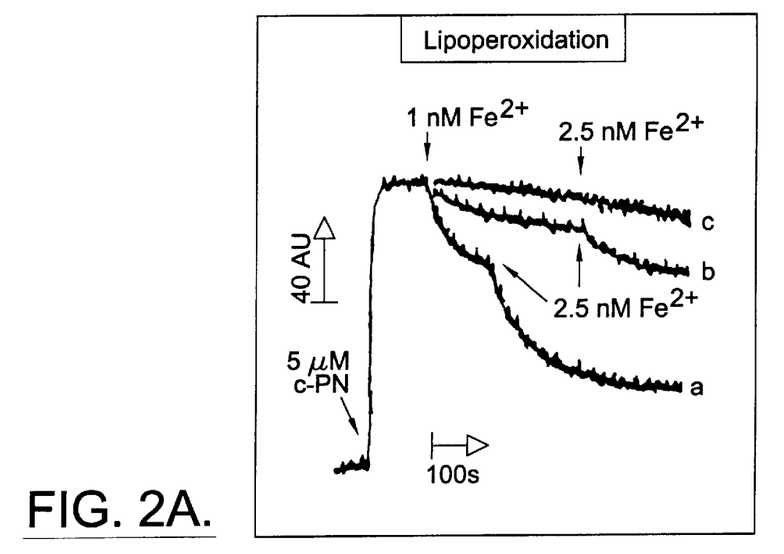

FIG. 2A shows the effect of quinone redox status on iron-induced lipoperoxidation. No protection could be observed when incubating heart homogenate with 60 μM oxidized idebenone for 3 min (trace a). Conversely, a significant protection was noted when in situ reduction of idebenone (providing about 2 μM of reduced idebenone) in the mitochondrial membrane was allowed by addition of succinate to the incubation medium prior to the addition of the c-PN probe (trace b). Increasing incubation time with succinate enhanced both reduction of idebenone (12 μM; 20% of total idebenone) and protection against lipoperoxidation (trace c).

Figure 2B:
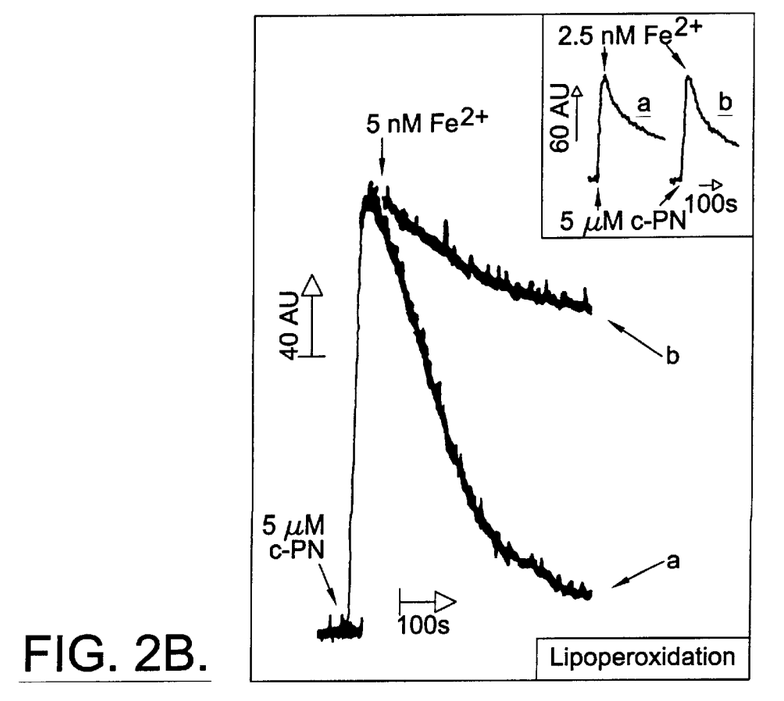

FIG. 2B shows the control of iron-induced lipoperoxidation by CoQ$_{10}$ (8 μM). In the absence of succinate, oxidized CoQ$_{10}$ did not protect from iron-induced lipoperoxidation (trace a). When CoQ$_{10}$ was reduced in situ by 3 min incubation with 10 mM succinate (trace b), a full protection against iron-induced lipoperoxidation was observed. Inset: Iron-induced peroxidation of liposomes carrying CoQ$_{10}$ (lipid bilayer devoid of the respiratory chain enzymes) was observed in both absence (trace a) and presence of succinate (trace b).

Figure 2C:
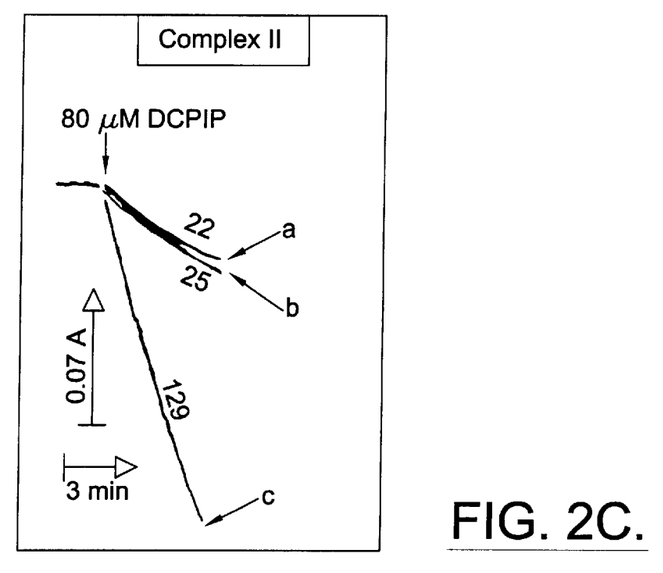

FIG. 2C shows the control of iron-induced damages to complex II activity by the redox status of quinone. Incubation of heart homogenate with either succinate (trace a) or 60 μM oxidized idebenone alone (trace b) did not protect complex II from iron induced damages. However, when succinate and idebenone were simultaneously added to the medium (20% of idebenone was reduced), a full protection of complex II activity was noted (trace c).

Figure 2D:
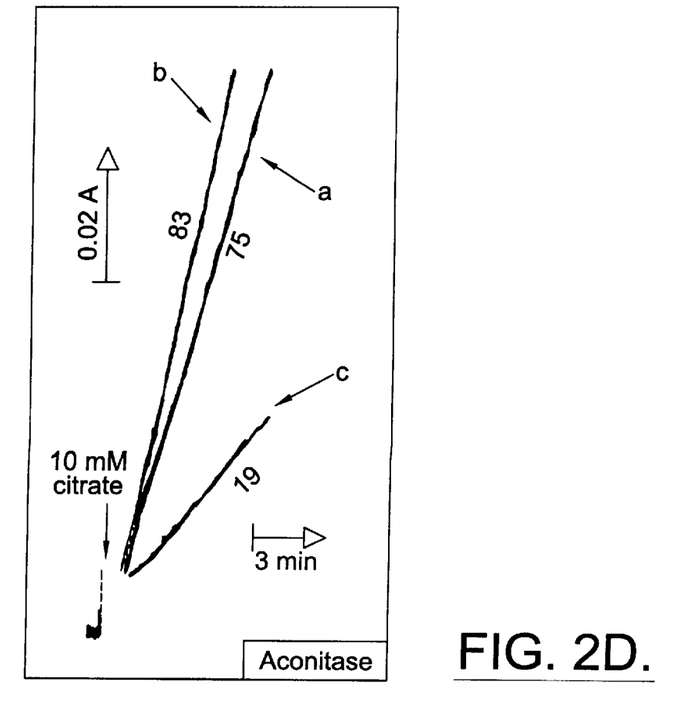

FIG. 2D shows the control of iron-induced damages to aconitase by the redox status of quinone. Heart homogenate (120 μg prot/ml) was first incubated for 3 min in 50 mM Tris-HCl buffer (pH 7.3) containing 5 nM Fe$^{2+}$, 8 μM CoQ$_{10}$, either in absence (trace c) or in presence of 10 mM succinate (trace a). Aconitase was assayed after additional 3 min incubation with 250 μM desferrixamine. Trace b: Aconitase activity measured after 6 min incubation in Tris-HCl buffer containing 250 μM desferrioxamine in the absence of Fe$^{2+}$.

The results of Table 2 represent the values of lipids peroxidation, complex II activity, and aconitase activity, determined in the same way as in Table 1 above. nm: not measured. SOD: superoxide dismutase.

TABLE 2

| | Iron-induced damages to: | | |
|---|---|---|---|
| Condition | Lipids | Complex II | Aconitases |
| 5 nM Fe$^{2+}$ + 60 μM idebenone | −63 ± 4 | −80 ± 3 | −2 ± 1 |
| 5 nM Fe$^{2+}$ + 50 μM CoQ$_4$ | −74 ± 3 | −81 ± 3 | 0 ± 0.4 |
| 5 nM Fe$^{2+}$ + 50 μM CoQ$_{10}$ | −66 ± 2 | −80 ± 2 | −1 ± 1 |
| 5 nM Fe$^{2+}$ + 10 mM succinate | −58 ± 3 | −77 ± 2 | nm |
| 5 nM Fe$^{2+}$ + 10 mM succinate + 60 μM idebenone | −1 ± 0.4 | −5 ± 1 | nm |
| 5 nM Fe$^{2+}$ + 10 mM succinate + 50 μM CoQ$_4$ | −1 ± 1 | −5 ± 2 | nm |
| 5 nM Fe$^{2+}$ + 10 mM succinate + 50 μM CoQ$_{10}$ | −1 ± 0.4 | −5 ± 1 | nm |
| 5 nM Fe$^{2+}$ + 2 nM EDTA + 60 μM idebenone | nm | nm | −81 ± 3 |
| 5 nM Fe$^{2+}$ + 2 nM EDTA + 10 mM succinate | nm | nm | −81 ± 2 |
| 5 nM Fe$^{2+}$ + 2 nM EDTA + 10 mM succinate + 60 μM idebenone | nm | nm | −86 ± 3 |

Interestingly, low concentrations of idebenone, reduced in situ by the respiratory chain, efficiently protected both membrane lipids and membrane-anchored complex II against iron injury (FIGS. 2A and C). A similar protection was provided by either succinate-reduced CoQ$_4$ (Table 2) or CoQ$_{10}$ (Table 2; FIG. 2B; note that markedly increased fluorescence signal observed in the presence of CoQ$_{10}$ should be ascribed to the fluorescent probe inserted into the CoQ$_{10}$-carrying liposomes). Oxidized quinone was ineffective (FIG. 2A, trace a; FIG. 2B, trace a; FIG. 2C, trace b) and succinate alone failed to protect membrane lipids against iron-induced peroxidation (FIG. 2B, inset).

Table 2 shows that neither succinate nor idebenone nor succinate+idebenone prevents the loss of aconitase activity induced by water-soluble chelators in the presence of reduced iron. However, (FIG. 2D) shows that. When the initial incubation medium was devoid of succinate, a 77% decrease of aconitase activity was observed (FIG. 2D, trace c). By contrast, a 3 min pre-incubation with succinate significantly protected aconitase activity (67%; FIG. 2D, trace a). It is worth noting that no decrease in enzyme activity was observed when the homogenate was pre-incubated with 200 μM desferrioxamine alone for 6 min (FIG. 2D, trace b). Quite similar data were obtained when EDTA was substituted to desferrioxamine (not shown). This shows that, beside their protective effect on membrane lipids and enzymes, quinones also indirectly protect soluble enzymes against iron-induced injury in in vitro system.

Example 3

Effect of Idebenone Administration on Cardiac Hypertrophy and Cerebellar Ataxia in Frda Patients Based on the previous in vitro data and owing to the innocuousness of the drug, five children ranging in age from 7½ to 14 years and two young adults ages 19 and 21 years, all diagnosed with FDRA, were given idebenone orally (5 mg/kg/day).

Figure 3:
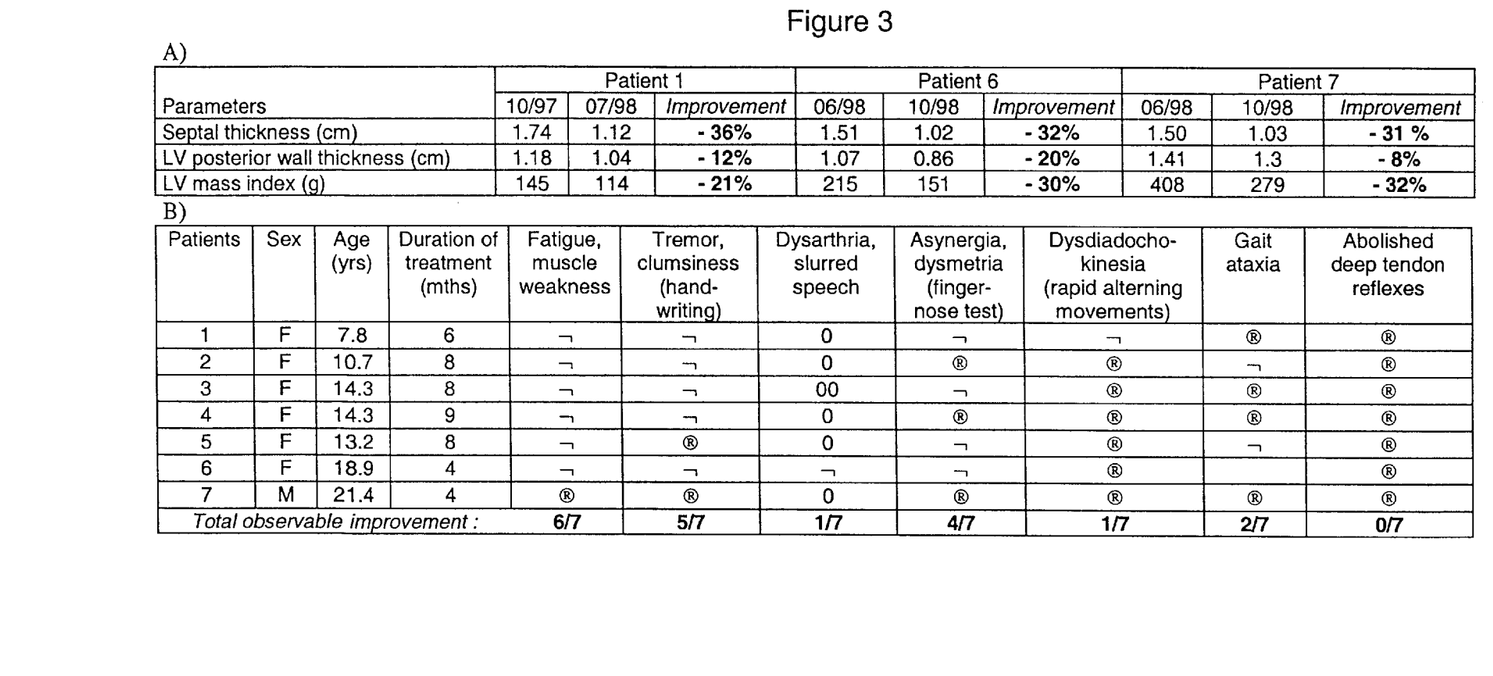
FIG. 3 summarizes the results of treatment of patients using the regime of the present invention.

The results observed after a course of treatment ranging from about 4 to about 9 months of administration at this dosage, are shown in FIG. 3:

A) Follow up of heart ultrasound parameters in patients 1, 6 and 7. LV: left ventricle. Note the decreased septal and left ventricle posterior wall thickness;

B) changes in cerebellar ataxia noted by parents and uninformed teachers. ⓡ: Unchanged; ¬: decrease; 0: No initial involvement.

These results show an improvement of muscle strength (5/5), delicate movements (handwriting; 4/5), asynergia/dysmetria (finger-nose test; 3/5), and gait ataxia was observed (2/5; FIG. 3B). Furthermore, a decrease hand clumsiness and an improvement of general condition was noted by the parents and uninformed teachers (FIG. 3B). Moreover, in three patients, quantitative evidence of drug efficiency was provided by the ultrasound observation of significant reduction of left ventricle wall (−8 to −20%) and septal thickness (−31 to −36%), resulting in a significant decrease of left ventricle mass index (−21 to −32%; FIG. 3A). However, deep tendon reflexes have not reappeared after a 9 month course of idebenone administration.

While the invention has been described by reference to several specific embodiments that have been described in considerable detail, the invention is not limited to the specific embodiments described. Those of ordinary skill in the art will recognize that the illustrative embodiments are susceptible to various modifications which are within the scope of the present invention. Accordingly, the scope of the invention is to be determined by reference to the following claims interpreted in light of the general principles of the invention as explained above.

What is claimed is:

1. A method of treating or preventing a disorder resulting from a mitochondrial dysfunction induced by an iron overload comprising administering an effective amount of an ubiquinone derivative.

2. The method of claim 1 wherein said ubiquinone derivative has the formula:

wherein R is linear or branched, saturated or unsaturated, aliphatic hydrocarbon or alcohol chain from 5 to 50 carbon atoms.

3. The method of claim 2 wherein R is linear or branched, saturated or unsaturated, aliphatic hydrocarbon or alcohol chain from 10 to 30 carbon atoms.

4. The method of claim 1 wherein said ubiquinone derivative is selected from the group consisting of idebenone, decylubiquinone, coenzyme Q2, coenzyme Q4, and coenzyme Q6.

5. The method of claim 1 wherein said effective amount ranges from about 1 mg/kg/day to about 50 mg/kg/day of ubiquinone derivative.

6. The method of claim 5 wherein said effective amount ranges from about 5 mg/kg/day to about 25 mg/kg/day.

7. The method of claim 1 in which said disorder results from an iron overload in Friedreich Ataxia.

8. The method of claim 7 wherein said disorder is hypertrophic cardiomyopathy.

9. The method of claim 1 in which said disorder results from an iron overload in Hallervorden-Spatz disease.

10. The method of claim 1 in which said disorder results from an iron overload in sideroblastic anemia.

11. The method of claim 1 further comprising administering a second therapeutic agent.

12. The method of claim 11 wherein said second therapeutic agent is a non-reducing antioxidant.

13. The method of claim 12 wherein said non-reducing antioxidant is α-tocopherol.

14. The method of claim 1 wherein said ubiquinone derivative is administered one or more times daily over at least 3 months.

15. The method of claim 14 wherein said ubiquinone derivative is administered one or more times daily over at least 6 months.

16. The method of claim 1 further comprising administering said ubiquinone derivative one or more times daily for about 4 to about 9 months.

17. A method of treating a disorder resulting from a mitochondrial dysfunction induced by an iron overload comprising administering to a patient suffering of said disorder an effective amount of an ubiquinone derivative selected from the group consisting of idebenone, decylubiquiqnone, coenzyme Q2, coenzyme Q4, and coenzyme Q6.

18. The method of claim 17 wherein said effective amount ranges from about 1 mg/kg/day to about 50 mg/kg/day of ubiquinone derivative.

* * * * *

UNITED STATES PATENT AND TRADEMARK OFFICE
CERTIFICATE OF CORRECTION

PATENT NO. : 6,133,322
DATED : October 17, 2000
INVENTOR(S) : Rustin et al.

It is certified that error appears in the above-identified patent and that said Letters Patent is hereby corrected as shown below:

Column 6, in the first formula, "$(CH_2)_n$" should read --$CH_2)_n$--.

Column 12, line 19, "decylubiquinone" should read --decylubiquiqnone--.

Signed and Sealed this

Eighth Day of May, 2001

*Attest:*

NICHOLAS P. GODICI

*Attesting Officer*  *Acting Director of the United States Patent and Trademark Office*